(12) United States Patent
An et al.

(10) Patent No.: US 10,912,520 B2
(45) Date of Patent: Feb. 9, 2021

(54) ACTIVITY LEVEL DETERMINATION FOR RISK STRATIFICATION

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Viktoria A. Averina, Roseville, MN (US); Yi Zhang, Plymouth, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1594 days.

(21) Appl. No.: 14/811,334

(22) Filed: Jul. 28, 2015

(65) Prior Publication Data

US 2016/0038094 A1 Feb. 11, 2016

Related U.S. Application Data

(60) Provisional application No. 62/033,257, filed on Aug. 5, 2014.

(51) Int. Cl.
*A61B 5/11* (2006.01)
*G16H 50/30* (2018.01)
(Continued)

(52) U.S. Cl.
CPC .......... *A61B 5/7275* (2013.01); *A61B 5/0255* (2013.01); *A61B 5/0432* (2013.01);
(Continued)

(58) Field of Classification Search
CPC ...... A61B 5/7232; A61B 5/7271–7296; A61B 5/1118; A61B 5/0205; A61B 5/02055;
(Continued)

(56) References Cited

U.S. PATENT DOCUMENTS 6,681,135 B1 * 1/2004 Davis .................. A61N 1/3655
607/21
8,241,223 B2 * 8/2012 Gavriely ................ A61B 7/003
327/40

(Continued)

OTHER PUBLICATIONS

Internet Archive, Healthline.com, "Congestive Heart Failure (CHF)" Jul. 10, 2013. Retrieved from https://web.archive.org/web/20130710032341/https://www.healthline.com/health/congestive-heart-failure (Year: 2013).*

(Continued)

*Primary Examiner* — David J. McCrosky
(74) *Attorney, Agent, or Firm* — Schwegman Lundberg & Woessner, P.A.

(57) ABSTRACT

In one example, a method of monitoring a sustained activity of a human or animal subject for the purpose of determining a risk group includes detecting a physical activity signal from the subject, determining a magnitude of the detected physical activity signal, initiating a timer in response to determining the magnitude of the physical activity signal exceeding an activity level threshold, triggering storing at least one value associated with the physical activity signal only when the magnitude of the physical activity signal exceeds the activity level threshold and the timer is greater than a duration threshold, and determining, using the processor circuit, an indication of the subject's cardiovascular disease based on the stored value.

16 Claims, 7 Drawing Sheets

(51) Int. Cl.
*A61B 5/00* (2006.01)
*A61B 5/103* (2006.01)
*A61B 5/0255* (2006.01)
*A61B 5/08* (2006.01)
*A61B 5/0432* (2006.01)
*A61B 5/0205* (2006.01)

(52) U.S. Cl.
CPC ............ *A61B 5/0803* (2013.01); *A61B 5/103* (2013.01); *A61B 5/1118* (2013.01); *A61B 5/002* (2013.01); *A61B 5/02055* (2013.01); *G16H 50/30* (2018.01)

(58) Field of Classification Search
CPC ...... A61B 5/0255; A61B 5/0002–0031; A61B 5/0432–04365; A61B 5/08; A61B 5/0803; A61B 5/0935; A61B 5/103; A61B 5/6869; A61B 5/7285; A61B 5/3956; A61B 5/046; A61B 5/0245; A61B 5/0022; A61B 5/7282; A61B 5/0456; A61B 5/021; A61B 5/0215; A61B 5/686; A61B 5/0816; A61B 5/7246; A61B 5/0031; A61B 5/1112–1118; A61B 5/112–1126; A61B 5/113; A61B 5/1135; A61N 1/3987; A61N 1/3956; A61N 1/36507; A61N 1/3624; G16H 50/30

USPC .................................................. 600/300, 301
See application file for complete search history.

(56) References Cited

U.S. PATENT DOCUMENTS

| | | | |
|---|---|---|---|
| 9,081,889 B2* | 7/2015 | Ingrassia, Jr. | A61B 5/1118 |
| 2008/0162182 A1 | 7/2008 | Cazares et al. | |
| 2008/0195165 A1* | 8/2008 | Stahmann | A61B 5/0215 607/18 |
| 2009/0069720 A1* | 3/2009 | Beck | A61B 5/1118 600/587 |
| 2013/0116578 A1 | 5/2013 | An et al. | |
| 2015/0351698 A1* | 12/2015 | Cronin | A61B 5/0022 600/485 |

OTHER PUBLICATIONS

Mathie, M. J., et al. "Detection of daily physical activities using a triaxial accelerometer." Medical and Biological Engineering and Computing 41.3 (2003): 296-301. (Year: 2003).*

Conraads, Viviane M., et al., "Physical Activity, Measured with Implanted Devices, Predicts Patient Outcome in Chronic Heart Failure", Online]. Retrieved from the Internet: <URL: http://circheartfailure.ahajournals.org/, (Accessed Feb. 9, 2015), 34 pgs.

* cited by examiner

ACTIVITY LEVEL DETERMINATION FOR RISK STRATIFICATION

CLAIM OF PRIORITY

This application claims the benefit of priority under 35 U.S.C. § 119(e) of U.S. Provisional Patent Application Ser. No. 62/033,257, filed on Aug. 5, 2014, which is herein incorporated by reference in its entirety.

TECHNICAL FIELD

This document pertains generally, but not by way of limitation, to techniques for measuring physical activity to determine risk stratification.

BACKGROUND

Between-patient diagnoses leverage previously recorded and documented patient data for the benefit of a current patient. By comparing the current patient to a group of similarly situated patients, probabilistic determinations may be made. For example, using one or more comparisons to a reference group, a particular patient may be probabilistically deemed more or less likely to experience a heart failure decompensation event in a given amount of time, e.g., within a year, relative to the reference group. Using one or more such probabilistic measurements, a physician may change diagnosis or adjust or adapt therapy to increase the quality of life of the particular patient. For example, a physician may increase the number of follow up visits or shorten the length of time between successive follow up visits, tune one or more thresholds on one or more alert methods, or alter medication to be more aggressive or less aggressive.

OVERVIEW

Because of various symptoms and increased efforts to reach normal activity level, heart failure patients often decrease their physical activity level during worsening of heart failure. As such, monitoring physical activity, e.g., using accelerometers, may be beneficial in quantifying a patient's risk of worsening heart failure. Currently, physical activity for risk stratification is monitored by accumulating all times that a patient spent above a threshold activity level, e.g., 25 milli-G (where G is equal to 9.81 m/s$^2$.)

The present inventors have recognized, among other things, that these physical activity monitoring techniques may be over-inclusive. In an example, the subject matter of this application can provide a solution to this problem, such as by monitoring a physical activity signal for a sustained period of time for the purpose of worsening heart failure risk stratification. The present inventors have recognized, for example, that some physical activity signals used in current risk stratification techniques are transient signals and not physiological. As such, those transient physical activity signals should be excluded. Using various techniques of this disclosure, physical activity signals that are not sustained for a duration threshold are excluded for risk stratification purposes.

In one example, the disclosure is directed to a machine-implemented method comprising detecting, using an activity sensor, a physical activity signal from a subject, determining, using a physiological signal processor circuit, a magnitude of the physical activity signal, initiating a timer in response to determining the magnitude of the physical activity signal exceeding an activity level threshold, triggering storing at least one value associated with the physical activity signal only when the magnitude of the physical activity signal exceeds the activity level threshold and the timer is greater than a duration threshold, and determining, using the processor circuit, an indication of the subject's cardiovascular disease based on the stored value.

In another example, the disclosure is directed to a system comprising an activity sensor configured to detect a physical activity signal from the subject, and a physiological signal processor circuit. The physiological signal processor circuit is configured to determine a magnitude of the physical activity signal, initiate a timer in response to detecting the magnitude of the physical activity signal exceeding an activity level threshold, trigger storing at least one value associated with the physical activity signal only when the magnitude of the physical activity signal exceeds the activity level threshold and the timer is greater than a duration threshold, and determine an indication of the subject's cardiovascular disease based on the stored value.

In another example, the disclosure is directed to a system comprising an activity sensor configured to detect a physical activity signal from the subject, and a physiological signal processor circuit. The physiological signal processor circuit is configured to determine a magnitude of the physical activity signal, compare the magnitude of the physical activity signal to a specified range of activity levels defined by a plurality of activity level thresholds, initiate a timer in response to detecting the magnitude of the physical activity signal falling within the specified range, accumulate an amount of time using the timer only when the magnitude of the physical activity signal falls within one of the plurality of specified ranges for the duration threshold, and determine an indication of the subject's risk based on the accumulated time including determining whether the subject is in one of at least two risk groups.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As indicated above, the present inventors have recognized, for example, that some physical activity signals used in current risk stratification techniques are transient signals and not physiological. Using various techniques of this disclosure, physical activity signals that are not sustained for a duration threshold are excluded for risk stratification purposes.

This disclosure describes two example techniques for monitoring physical activity of a subject: an active time implementation and a maximum level implementation. The active time implementation is described in detail below with respect to FIGS. 3 and 6, for example. In general, the active time implementation involves accumulating the time that a subject's physical activity level signal both exceeds an activity level threshold and exceeds a duration threshold, and not including any time that the magnitude of the subject's physical activity signal exceeds the activity level threshold for less than the duration threshold.

The maximum level implementation for monitoring physical activity of a subject also involves ensuring that the physical activity level signal is present for a sustained period of time before including the signal as part of a subject's activity, like the active time implementation. In general, the maximum level implementation involves determining a maximum physical activity level achieved by a subject, e.g., within a 24-hour period, that exceeded a duration threshold, e.g., 8 minutes. The maximum level implementation is described in detail below with respect to FIGS. 7 and 8.

Figure 1:
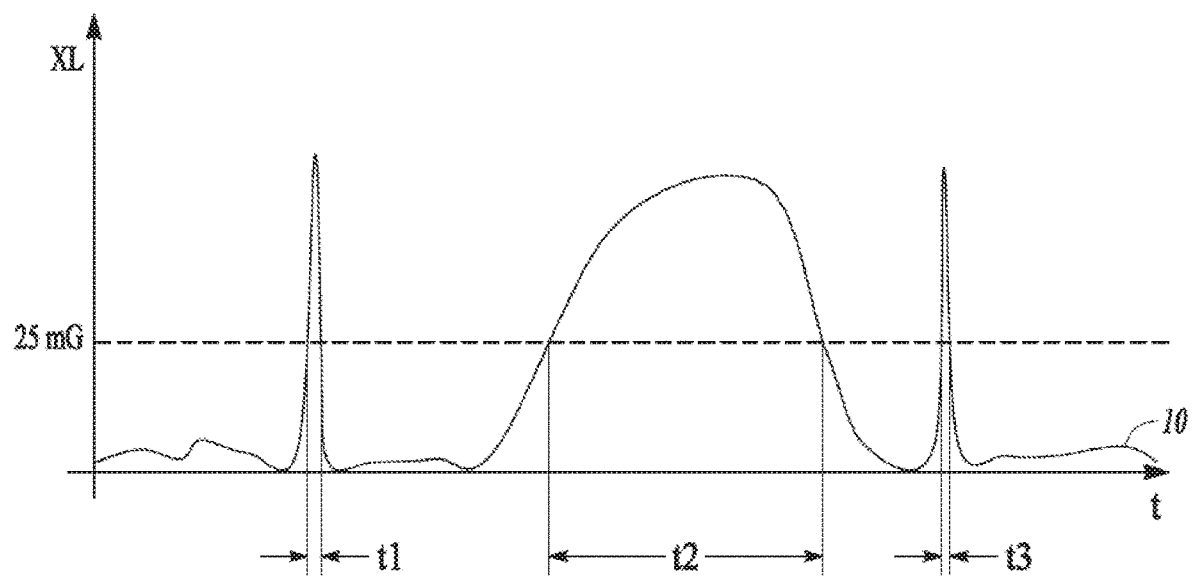
FIG. 1 is a graph illustrating an existing technique for monitoring physical activity of a patient.

FIG. 1 is a graph illustrating an existing technique for monitoring physical activity of a patient. In FIG. 1, the x-axis represents time in seconds and the y-axis represents activity level (XL) in milli-Gravity (mG). As seen in FIG. 1, a physical activity signal 10 of a patient exceeds an activity level threshold, e.g., 25 mG, for three time periods, namely time periods t1, t2, and t3, over a monitoring time frame. The time periods t1 and t3 are both of short duration when compared to the time period t2. In some examples, the activity level threshold is between about 10 mG (0.0981 m/s$^2$) and about 50 mG (0.4905 m/s$^2$), preferably between about 15 mG and about 45 mG. In one example, the activity level threshold is about 33.6 mG.

Using existing techniques, the patient's total accumulated physical activity during the monitoring time frame is equal to the sum of all time periods in which the physical activity signal exceeds an activity level threshold. In FIG. 1, the patient's total accumulated physical activity is equal to t1+t2+t3. That is, physical activity is accumulated as long as the signal level is above a threshold, e.g., 25 mG, regardless of the duration of the signal above the activity level threshold.

Figure 2A:
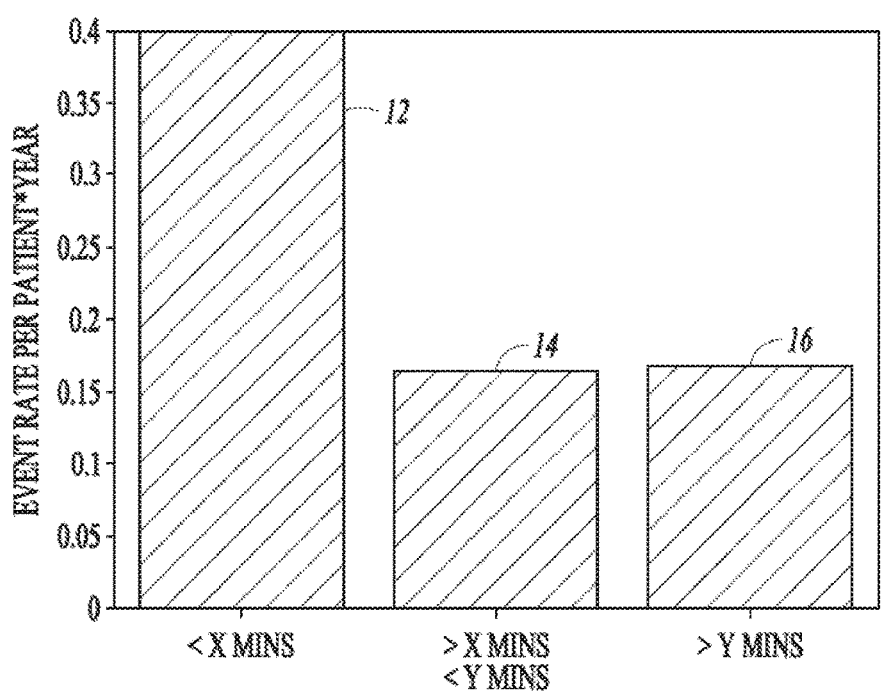
FIG. 2A is a bar graph depicting an event rate between multiple groups of patients using the existing technique of FIG. 1 for monitoring physical activity of a patient.

FIG. 2A is a bar graph depicting an event rate between multiple groups of patients using the existing technique of FIG. 1 for monitoring physical activity of a patient. The y-axis represents the event rate per patient*year, and the x-axis represents bins of time associated with the accumulated time patients spent above the activity level threshold.

The bar graph in FIG. 2A depicts 3 bars, namely bars 12, 14, and 16. The left-most bar 12 is associated with patients having the lowest accumulated physical activity of less than X minutes, e.g., less than about 67 minutes of physical activity per day. The right-most bar 16 is associated with patients having the highest accumulated physical activity of greater than Z minutes, e.g., greater than about 110 minutes per day. The middle bar 14 is associated with patients having accumulated physical activity between X minutes and Y minutes, e.g., about 67 minutes and 110 minutes per day. Thus, the bars 12, 14, and 16 represent low, middle, and high physical activity level groups, respectively.

As seen in bar 12 of FIG. 2A, the event rate is much higher at the end of a year, e.g., 0.4, for patients having the lowest accumulated physical activity per day. The event rate associated with the bars 14, 16, however, is significantly lower than the bar 12, but the bars 14, 16 do not show much separation between one another, e.g., each having an event rate between 0.15 and 0.2.

Figure 2B:
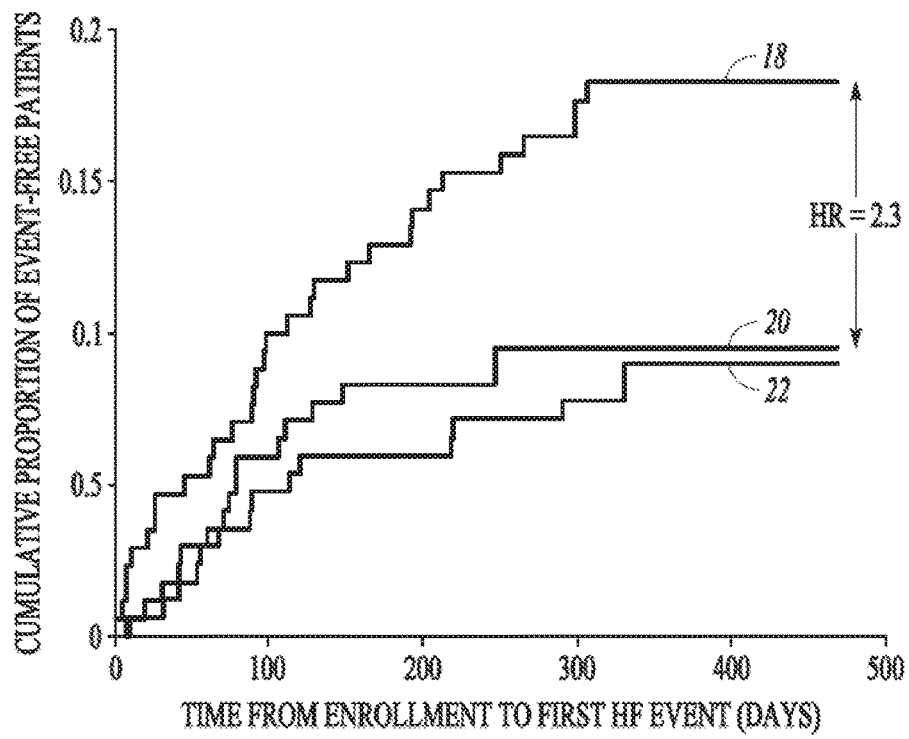
FIG. 2B is a graph illustrating a stratification of physical activity level data for multiple patients using the existing technique of FIG. 1

FIG. 2B is a graph illustrating a stratification of physical activity level data for multiple patients using the existing technique of FIG. 1. In an example, the physical activity of 1000 patients was monitored and the first 30 days of each patient's physical activity level data was collected. The data was divided into 3 equal-sized groups based on whether the physical activity level was a low physical activity level of less than X minutes, e.g., less than about 67 minutes of physical activity per day, medium physical activity level of between X minutes and Y minutes, e.g., between about 67 minutes and 110 minutes per day, and high physical activity level of greater than Y minutes, e.g., greater than about 110 minutes per day. The data of the 3 groups is shown in FIG. 2B and is used to predict a likelihood, or risk, of heart failure decompensation. In another example, a set of thresholds used to separate multiple physical activity level groups were chosen empirically.

In FIG. 2B, the x-axis represents the time from enrollment to the first heart failure (HF) event in days, and the y-axis represents the cumulative proportion of event free patients. The low physical activity level group is represented by line 18, the medium physical activity level group is represented by line 20, and the high physical activity level group is represented by 22. As seen in FIG. 2B, by the end of the year, about 20% of the low physical activity level group represented by line 18 may have at least one HF decompensation event. In contrast, by the end of the year, about 10% of the high physical activity level group represented by line 22 may have at least one HF decompensation event.

The hazard ratio is a risk ratio between the high physical activity level group and the low physical activity level group. In FIG. 2B, the hazard ratio is 2.3, so a person in the low physical activity level group is 2.3 times more likely to have an HF decompensation event during the next year than a person in the high physical activity level group. A larger hazard ratio represents a larger separation between groups. A larger separation between groups may result in a clinician being more likely to accurately adjust his/her management of a patient within one of the three groups. For example, it may be desirable for a clinician to have a follow-up visit with a patient in the high physical activity level group every 6 months, but follow-up with a patient in the low physical activity level group more frequently, e.g., every 3 months. As seen in FIG. 2B, however, the separation between groups 20 and 22 is so small that a clinician may not be able to adjust his/her management of the patient in a meaningful way. Using various techniques of this disclosure described below, the hazard ratio may be increased and better separation between groups of patients may be achieved by ensuring that physical activity signals that are not sustained for a duration threshold are excluded for risk stratification purposes.

Figure 3:
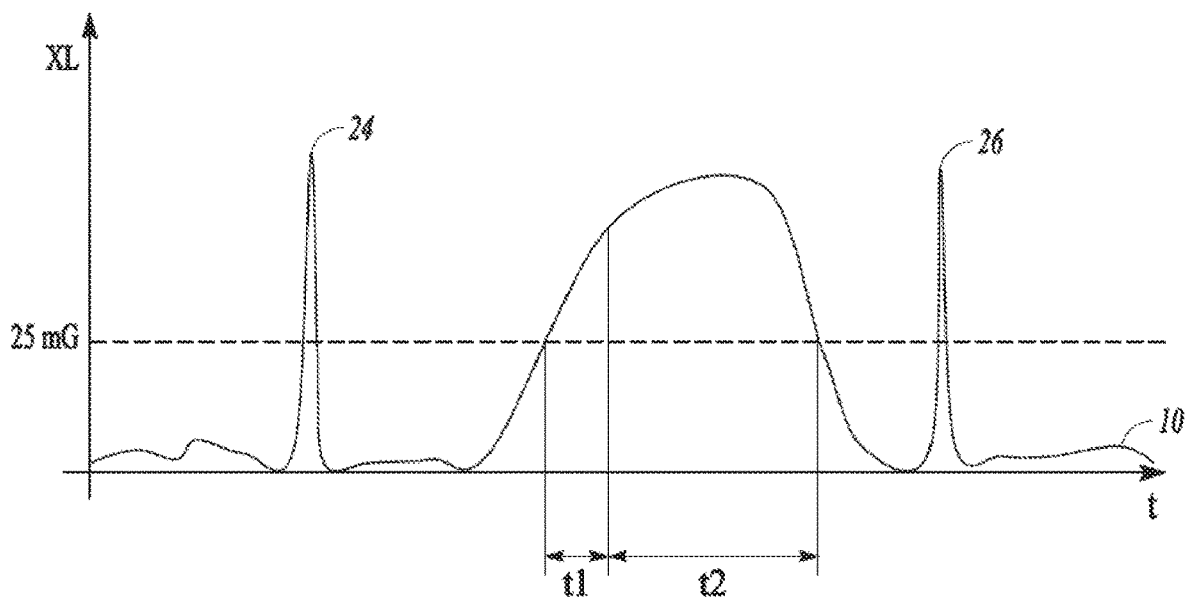
FIG. 3 is a graph illustrating a technique for monitoring physical activity of a patient, in accordance with this various techniques of this disclosure.

FIG. 3 is a graph illustrating a technique for monitoring physical activity of a patient, in accordance with this various techniques of this disclosure. In FIG. 3, the x-axis represents time in seconds and the y-axis represents activity level (XL) in mG. FIG. 3 depicts the physical activity signal 10 of FIG. 1.

In accordance with this disclosure, it is desirable that the physical activity signal 10 be sustained above a physical activity level threshold, e.g., 25 mG in the example of FIG. 3, and for a time exceeding a duration threshold of t1, e.g., about 30 seconds to about 90 seconds, in order to be included in the physical activity calculation. As such, in FIG. 3, time t2 is included in the physical activity calculation because over the period of time t2, the physical activity signal both exceeded a physical activity level threshold, e.g., 25 mG, and exceeded the duration threshold of t1. In some example implementations, both the duration threshold t1 and the physical activity signal time t2 can be included in the physical activity calculation. That is, the activity level time in FIG. 3 equals t1+t2. In other examples, the activity level time in FIG. 3 equals t2.

In contrast to the existing technique described above with respect to FIG. 1, transients 24, 26 of the physical activity signal 10 are excluded from the calculation of a patient's total accumulated physical activity during the monitoring time frame because the transients 24, 26 are not sustained above a physical activity level threshold, e.g., 25 mG in the example of FIG. 3, and beyond the duration threshold of t1. As shown graphically below with respect to FIGS. 4A and 4B, by excluding any transients, using various techniques described in this disclosure, a patient's physical activity level can be accurately categorized, thereby allowing a clinician to accurately assess their risk of worsening heart failure.

Figure 4A:
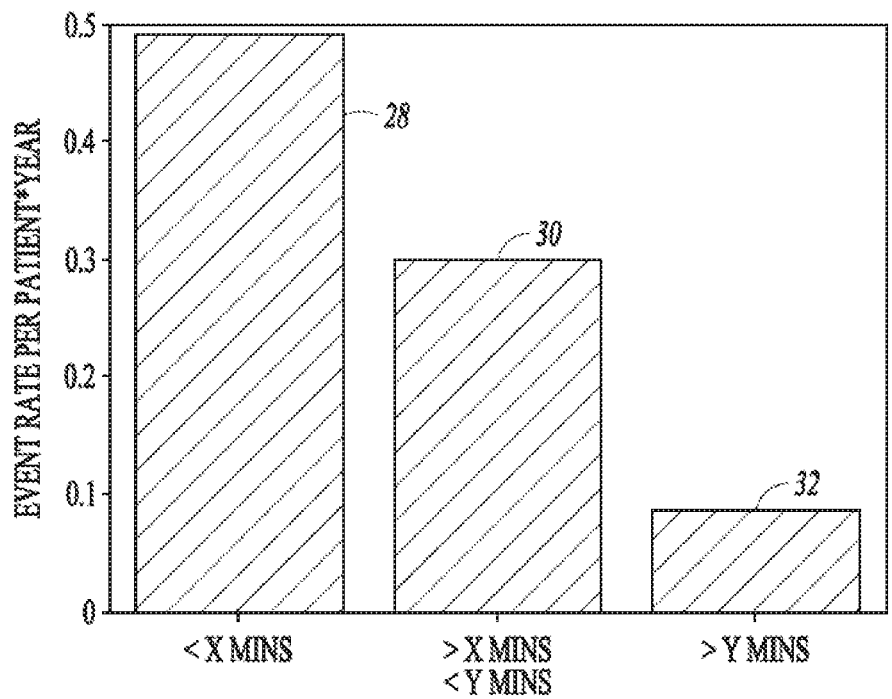
FIG. 4A is a bar graph depicting an event rate between multiple groups of patients using the technique for monitoring physical activity of a patient of FIG. 3, in accordance with this disclosure.

FIG. 4A is a bar graph depicting an event rate between multiple groups of patients using the technique for monitoring physical activity of a patient of FIG. 3, in accordance with this disclosure. The y-axis represents the event rate per patient*year, and the x-axis represents bins of time associated with the accumulated time patients spent above the activity level threshold.

The bar graph in FIG. 4A depicts 3 bars, namely bars 28, 30, and 32. The left-most bar 28 is associated with patients having the lowest accumulated physical activity of less than X minutes, e.g., less than about 25 minutes of physical activity per day. The right-most bar 32 is associated with patients having the highest accumulated physical activity of greater than Y minutes, e.g., greater than about 65 minutes per day. The middle bar 30 is associated with patients having accumulated physical activity between X minutes and Y minutes, e.g., about 25 minutes and about 65 minutes per day. Thus, the bars 28, 30, and 32 represent low, middle, and high physical activity level groups.

As seen in bar 28 of FIG. 4A, the event rate is much higher, e.g., 0.5, for patients having the lowest accumulated physical activity per day. The event rate associated with the bars 30, 32, however, is significantly lower than the bar 28. In contrast to the bars 12, 14, and 16 in FIG. 2A, the bars 28, 30, and 32 in FIG. 4A are more clearly separated from one another, in particular the bars 30, 32.

The separation between the bars 28, 30, and 32 of FIG. 4A represents the true separation between low, medium, and high physical activity groups, in contrast to the bars 12, 14, and 16 of FIG. 2A. That is, if any transients, e.g., physical activity signals that are not sustained above a physical activity level threshold and beyond a duration threshold, are included in the physical activity signal and are used in the calculation of a patient's total accumulated physical activity during the monitoring time frame, as is done with the existing technique depicted in FIGS. 1-2B, it is possible for a patient to be inaccurately switched from their actual first physical activity group, e.g., low physical activity group, into a second physical activity group, e.g., higher physical activity group, due to the transients in the physical activity signal, e.g., accelerometer signal. However, by excluding any transients, e.g., physical activity signals that are not sustained above a physical activity level threshold and beyond a duration threshold, using various techniques described in this disclosure, a patient's physical activity level can be accurately categorized, thereby allowing a clinician to accurately assess their risk of worsening heart failure.

Figure 4B:
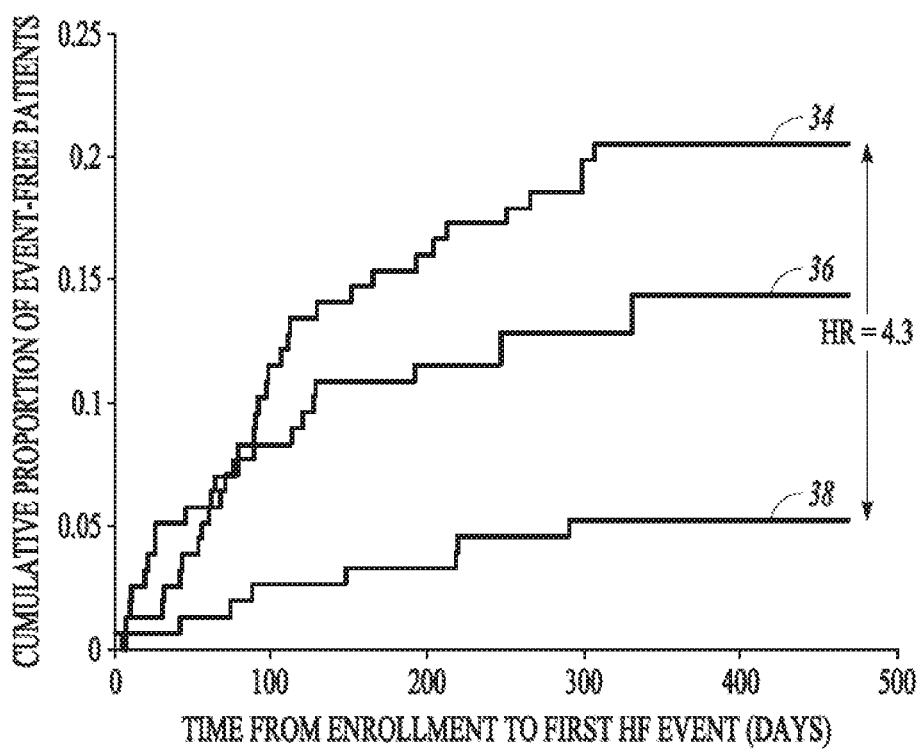
FIG. 4B is a graph illustrating a stratification of physical activity level data for multiple patients using the technique for monitoring physical activity of a patient of FIG. 3, in accordance with this disclosure.

FIG. 4B is a graph illustrating a stratification of physical activity level data for multiple patients using the technique for monitoring physical activity of a patient of FIG. 3, in accordance with this disclosure. The physical activity of 1000 patients, for example, was monitored and the first 30 days of each patient's physical activity level data was collected. The data was divided into 3 equal-sized groups based on whether the physical activity level was a low physical activity level of less than X minutes, e.g., less than about 25 minutes of physical activity per day, medium physical activity level of between Z minutes and Y minutes, e.g., between about 25 minutes and 65 minutes per day, and high physical activity level of greater than Y minutes, e.g., greater than about 65 minutes per day. The data of the 3 groups is shown in FIG. 4B and is used to predict a likelihood, or risk, of heart failure decompensation.

In FIG. 4B, the x-axis represents the time from enrollment to the first heart failure (HF) event in days, and the y-axis represents the cumulative proportion of event free patients. The low physical activity level group is represented by line 34, the medium physical activity level group is represented by line 36, and the high physical activity level group is represented by 38.

By excluding any transients, e.g., physical activity signals that are not sustained above a physical activity level threshold and beyond a duration threshold, using various techniques described in this disclosure, the hazard ratio increased from 2.3 in FIG. 2B to 4.3 in FIG. 4B, which indicates much better separation between the low physical activity level group 34 and the high physical activity level group 38.

In addition, by excluding any transients in the physical activity signal, the separation between the low physical activity level group 34, the medium physical activity level group 36, and the high physical activity level group 38 greatly improved. As seen in FIG. 4B, by the end of the year, about 20% of the low physical activity level group represented by line 34 may have at least one HF decompensation event, about 15% of the medium physical activity level group represented by line 36 may have at least one HF decompensation event, and about 5% of the high physical activity level group represented by line 38 may have at least one HF decompensation event.

As mentioned above, a larger separation between groups may result in a clinician being more likely to accurately adjust his/her management of a patient within one of the three groups. The separation between groups 34, 36 and 38 in FIG. 4B is much better than the separation between groups 18, 20 and 22 in FIG. 2B, particularly between the high physical activity level group 38 and the medium physical activity level group 36. Thus, by excluding any transients, in accordance with this disclosure, patient physical activity level can be accurately categorized into a first physical activity group, e.g., low physical activity group, that reflects the patient's actual physical and not inaccurately categorized into a higher physical activity group, due to the inclusion of transients in the physical activity signal, e.g., accelerometer signal.

Figure 5:
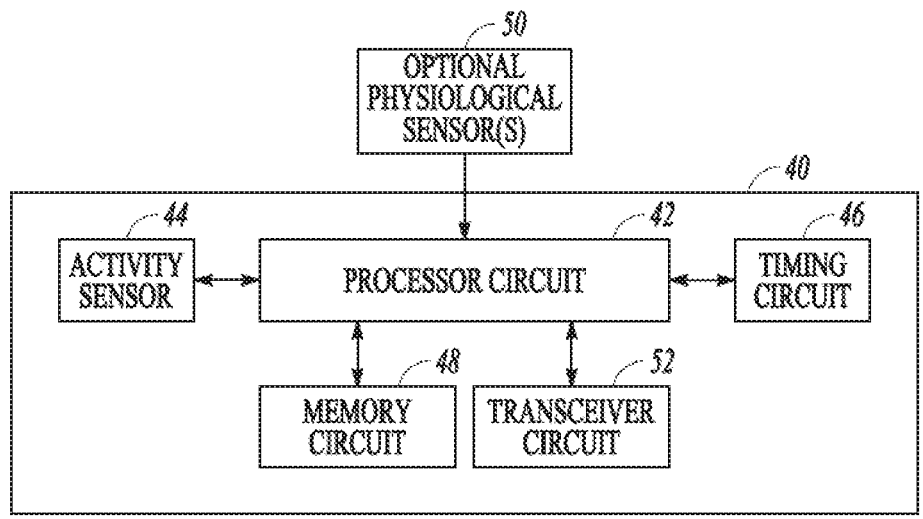
FIG. 5 is a flow diagram of an example of a technique for monitoring physical activity of a patient, in accordance with this disclosure.

FIG. 5 is a block diagram of an example of a device that can be used to implement various techniques of this disclosure. A patient device 40 (referred to generally in this disclosure as "device 40") can include an activity sensor, e.g., an accelerometer, for detecting a physical activity of a subject and generating a signal indicative of the detected physical activity. A physiological signal processor circuit 42 (also referred to in this disclosure as a "processor circuit") of the device 40 can receive the physical activity signal generated by the activity sensor 44. Upon receiving the physical activity signal, the processor circuit 42 can determine a magnitude of the detected physical activity signal and can initiate a timer of timing circuit 46 in response to detecting the magnitude of the physical activity signal exceeding an activity threshold. A memory circuit 48 can accumulate or store timing information and magnitude information associated with the detected physical activity signal. In accordance with this disclosure, timing information is accumulated or stored when the time that the detected physical activity signal is present is greater than a duration threshold, e.g., about 30 seconds to about 90 seconds, and not when the time that the detected physical activity signal is present is less than the duration threshold. Based on the accumulated or stored timing information, the processor circuit 42 can determine an indication of the subject's cardiovascular disease, e.g., heart failure risk or status, risk of decompensating, patient health, etc. For example, the processor circuit 42 can determine that the subject is in one of two or more physical activity groups, which is an indication of the subject's risk. In one example, the processor can determine that the subject is in one of three physical activity groups: a low physical activity group, a medium physical activity group, or a high physical activity group, which is an indication of the subject's risk, e.g., of heart failure. It may be desirable to include more stratification and provide more than three physical activity groups. In another example, the processor circuit 42 can determine a risk percentage.

Various physiological sensors 50 may optionally be used to confirm that the subject is active. The physiological sensors 50 may include, for example, a body temperature sensor, a heart sounds sensor, e.g., for measuring a first heart sound $S_1$, a heart rate sensor, and respiration sensors for measuring respiration rate, tidal volume, and minute ventilation of the subject. Each of these sensors can be used to supplement the information provided by the activity sensor, e.g., accelerometer, to assist the processor circuit 42 exclude transient signals.

For example, when the activity level signal exceeds an activity level threshold, one or more of the various physiological sensors 50 can be used to confirm that the subject is active. In one example, $S_1$ and heart rate may increase, which can indicate increased cardiac output associated with higher metabolic demands. In another example, respiratory rate, tidal volume and minute ventilation may increase indicating increased breathing efforts. In another example, a patient's body temperature may increase indicating an increased muscle heat production.

The processor circuit 42 is capable of being implemented using hardware, software, and combinations of hardware and software. According to various example configurations, the processor circuitry can execute instructions embedded in the memory, e.g., memory circuit 48, to perform functions described throughout this disclosure. The device 40 can also include a transceiver circuit 52 for use in communicating with a programmer or another external or internal device. Various configurations include wireless communication capabilities. For example, some transceiver embodiments use a telemetry coil to wirelessly communicate with a programmer or another external or internal device.

In some example configurations, the device 40 can be an implantable medical device. In other examples, the device 40 can be a device worn externally by the subject, e.g., around the subject's wrist.

Figure 6:
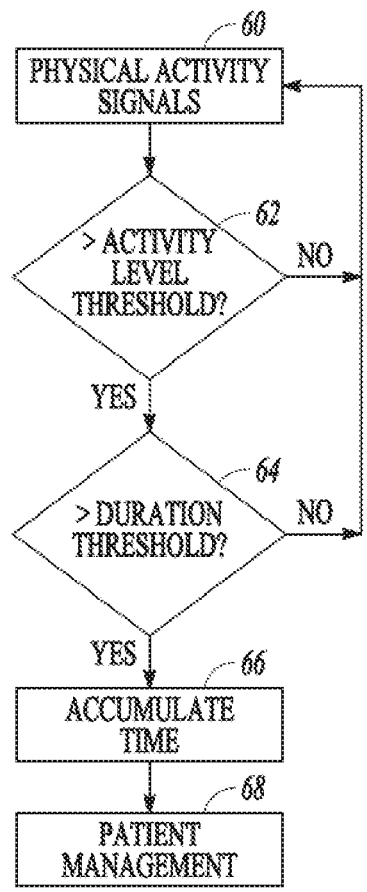
FIG. 6 is a flow diagram of an example of a technique for monitoring physical activity of a patient, in accordance with this disclosure.

FIG. 6 is a flow diagram of an example of a technique for monitoring physical activity of a patient, in accordance with this disclosure. In FIG. 6, a physical activity sensor, e.g., physical activity sensor 44 of FIG. 5 such as an accelerometer can detect a physical activity of a subject and generate a physical activity signal representing the physical activity (block 60). A processor, e.g., physiological signal processor circuit 42 of FIG. 5, can determine a magnitude of the physical activity signal. The processor can compare the determined physical activity signal magnitude to an activity level threshold, e.g., 25 mG in the example of FIG. 3 (block 62).

If the determined magnitude does not exceed the activity level threshold ("NO" branch of block 62), then the processor can return to the beginning of the flow diagram and wait for the next detected physical activity signal (block 60). If the determined magnitude exceeds the activity level threshold ("YES" branch of block 62), then the processor can proceed to the next block (block 64). At block 64, the processor can initiate a timer, e.g., using timing circuit 46, and can determine whether the physical activity signal exceeds a duration threshold, e.g., about 30 seconds to about 90 seconds.

If the detected physical activity signal does not exceed the activity level threshold for a time greater than the duration threshold ("NO" branch of block 64), then the processor can return to the beginning of the flow diagram and wait for the next detected physical activity signal (block 60). However, if the detected physical activity signal does exceed the activity level threshold for a time greater than the duration threshold ("YES" branch of block 64), then the processor can begin accumulating an amount of time, which can be used to determine a total physical activity level of the subject (block 66). Based on the determined total physical activity level of the subject, the processor can determine an indication of risk, e.g., low/medium/high physical activity group (block 68), for heart failure for example. In some examples, the device 40 can transmit the indication to another device, e.g., using the transceiver circuit 52 of FIG. 5.

As indicated above, this disclosure describes two example techniques for monitoring physical activity of a subject: an active time implementation and a maximum level implementation. The active time implementation was described in detail above with respect to FIGS. 3 and 6, for example.

Like the active time implementation, the maximum level implementation for monitoring physical activity of a subject also involves ensuring that the physical activity level signal is present for a sustained period of time before including the signal as part of a subject's activity. In general, the maximum level implementation involves determining a maximum physical activity level achieved by a subject, e.g., within a 24-hour period, after any transients have been removed (first duration threshold), that exceeded another, second duration threshold, e.g., 0 minutes to 10 minutes. The second duration threshold can vary from 0 minutes (because any transition periods or transients have already been removed) to a fixed number, e.g. 10 minutes.

Figure 7:
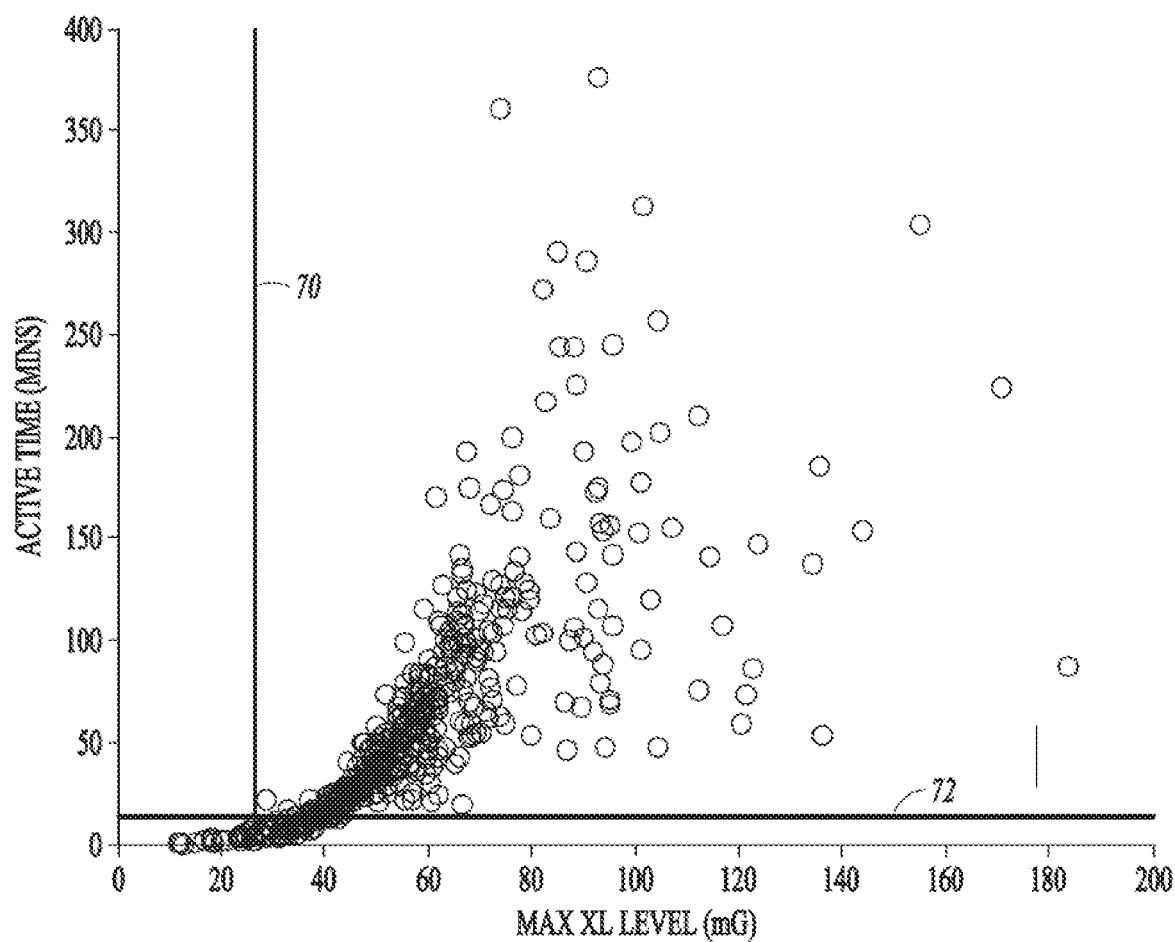
FIG. 7 is a graph depicting an example of a scatterplot that correlates the active time implementation and the maximum level implementation.

FIG. 7 is a graph depicting an example of a scatterplot that correlates the active time implementation and the maximum level implementation. The x-axis represents maximum activity level ("Max XL level") in mG and the y-axis represents active time in minutes. The scatterplot indicates that the two techniques are highly correlated. The maximum level implementation is described in detail below with respect to FIG. 8.

The active time implementation and the maximum level implementation can be visualized using the scatterplot of FIG. 7 and two lines 70, 72. The active time implementation, described above, can be visualized using the vertical line 70, which represents an activity level threshold, e.g., about 25 mG in FIG. 7. The subject's activity level can be determined by integrating all the time for each data point on the right side of the activity level threshold, or line 70.

The maximum level implementation can be visualized using the horizontal line 72, which represents a second duration threshold, e.g., about 8 minutes in FIG. 7. The subject's maximum level can be determined by determining the data point with the maximum activity level that is above the second duration threshold, or line 72. The maximum level implementation is described in detail below with respect to FIG. 8.

Figure 8:
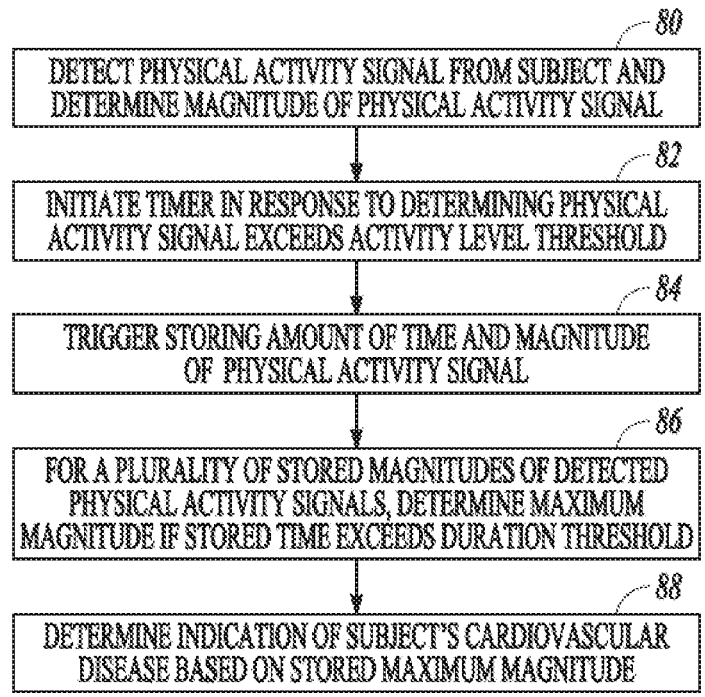
FIG. 8 is a flow diagram of another example of a technique for monitoring physical activity of a patient, in accordance with this disclosure.

FIG. 8 is a flow diagram of another example of a technique for monitoring physical activity of a patient, in accordance with this disclosure. In FIG. 8, a physical activity sensor, e.g., physical activity sensor 44 of FIG. 5 such as an accelerometer, can detect a physical activity of a subject, generate a physical activity signal representing the physical activity, and determine a magnitude of the physical activity signal (block 80). At block 82, a processor, e.g., processor circuit 42 of FIG. 5, can initiate a timer, e.g., using timing circuit 46 of FIG. 5, in response to determining that the magnitude of the physical activity signal exceeds an activity level threshold. The processor can trigger storing in a memory, e.g., memory circuit 48 of FIG. 5, an amount of time determined by the timer and the magnitude associated with the detected physical activity signal (block 86). For example, the processor may store pairs of data points in memory, namely an amount of time that a subject spent at an activity level and the magnitude of the activity level.

After some period of time, e.g., a 24-hour period, the processor can determine a maximum magnitude if the stored time has exceeded a second duration threshold, e.g., about 0 minutes to about 10 minutes, for a plurality of stored magnitudes of detected physical activity level signals (block 88). In some example implementations, the second duration threshold can be about 8 minutes. Then, the processor can determine an indication of the subject's cardiovascular disease, e.g., heart failure risk or status, risk of decompensating, patient health, etc., based on the stored maximum magnitude (block 90). In some example implementations, the processor can determine an X-day average of the daily maximum magnitudes, where X can vary from 3 days to 120 days, and determine an indication of the subject's heart failure risk, e.g., one of at least two risk groups, such as low/medium/high physical activity group. In some examples, the device 40 can transmit the indication to another device, e.g., using the transceiver circuit 52 of FIG. 5.

Figure 9:
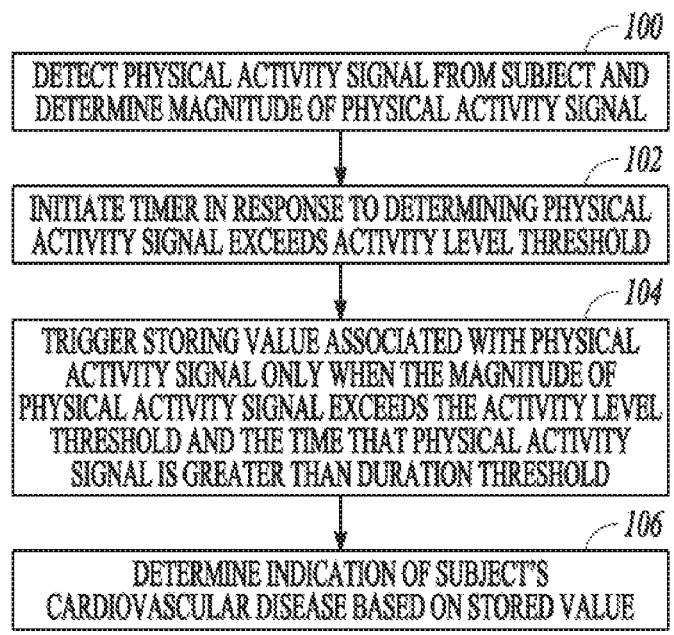
FIG. 9 is a flow diagram of an example of a technique for monitoring physical activity of a patient, in accordance with this disclosure.

FIG. 9 is a flow diagram of an example of a technique for monitoring physical activity of a patient, in accordance with this disclosure. More particularly, the flow diagram FIG. 9 generalizes the active time implementation and the maximum level implementations of FIGS. 6 and 8, respectively.

In FIG. 9, a physical activity sensor, e.g., physical activity sensor 44 of FIG. 5 such as an accelerometer, can detect a physical activity of a subject, generate a physical activity signal representing the physical activity, and determine a magnitude of the physical activity signal (block 100). At block 102, a processor, e.g., processor circuit 42 of FIG. 5, can initiate a timer, e.g., using timing circuit 46 of FIG. 5, in response to determining that the magnitude of the physical activity signal exceeds an activity level threshold.

The processor can and trigger storing in a memory, e.g., memory circuit 48 of FIG. 5, a value associated with the detected physical activity signal, e.g., time (active time implementation) and/or magnitude (maximum level implementation), only when the magnitude of the physical activity signal exceeds the activity level threshold and time that the physical activity signal is present is greater than a duration threshold, and not when the time that the detected physical activity signal is present is less than the duration threshold (block 106). For example, in the active time implementation, the processor can determine a magnitude of the physical activity signal and if it is greater than an activity level threshold, the processor can begin accumulating time, e.g., in memory, only when the time that the detected physical activity signal is present is greater than a first duration threshold, e.g., about 30 seconds to about 90 seconds, and not when the time that the detected physical activity signal is present is less than the duration threshold. As another example, in the maximum level implementation, the processor can store a magnitude of the physical activity signal and, in some examples, the time that the physical activity level maintained that magnitude, when the time that the detected physical activity signal is present is greater than a second duration threshold, e.g., about 0 minutes to about 10 minutes, and not when the time that the detected physical activity signal is present is less than the duration threshold.

Then, the processor can determine an indication of the subject's cardiovascular disease, e.g., heart failure risk or status, risk of decompensating, patient health, etc., based on the stored value, e.g., one of at least two risk groups, such as low/medium/high physical activity group (block 108). In some examples, the device 40 can transmit the indication to another device, e.g., using the transceiver circuit 52 of FIG. 5.

Figure 10:
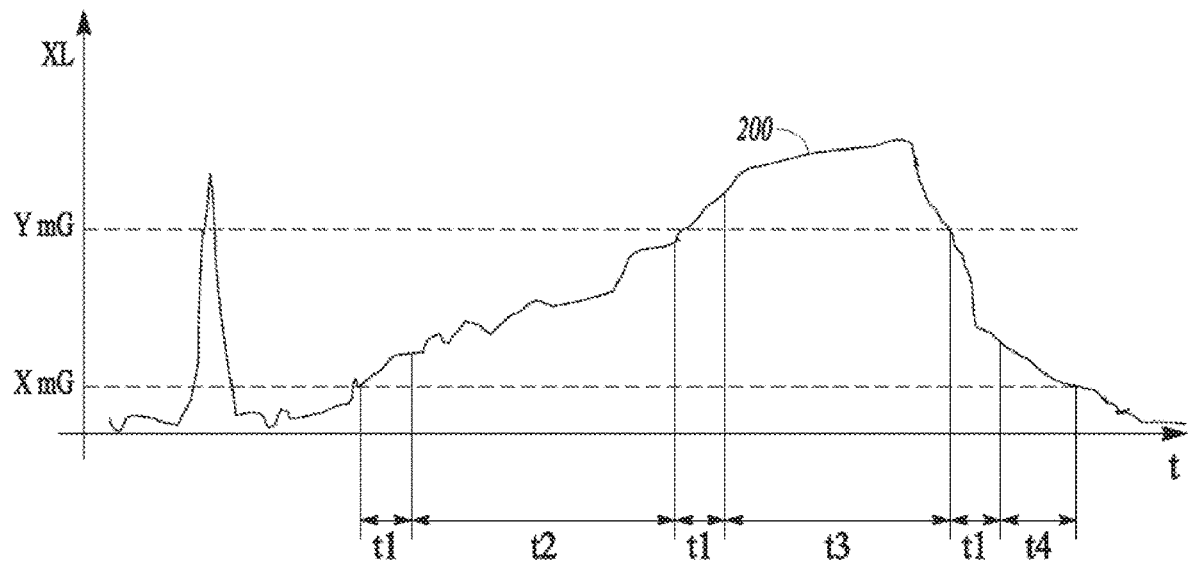
FIG. 10 is a graph illustrating another technique for monitoring physical activity of a patient, in accordance with this various techniques of this disclosure.

FIG. 10 is a graph illustrating another technique for monitoring physical activity of a patient, in accordance with this various techniques of this disclosure. In FIG. 10, the x-axis represents time in seconds and the y-axis represents activity level (XL) in mG. FIG. 10 depicts another physical activity signal 200.

In contrast to the graph shown in FIG. 3, the graph of FIG. 10 includes first and second physical activity level thresholds, namely X mG and Y mG, e.g., about 11 mG and about 22 mG. In other example implementations, there may be three (3) or more physical activity level thresholds. For example, in some examples, there may be a third physical activity level threshold of Z mG, e.g., about 33 mG. The two (or more) physical activity level thresholds can be used to "bin" activity within a specified range (or ranges) of activity levels. For example, a processor circuit can compare a determined magnitude of the physical activity signal 200 to a specified range of physical activity level thresholds, e.g., a range of X mG to Y mG as shown in FIG. 10, and bin the physical activity within a specified range.

As seen in FIG. 10, the activity level signal 200 crosses the two physical activity level thresholds X mG and Y mG as the signal 200 increases and as the signal 200 decreases. In accordance with this disclosure, it may be desirable that any transition periods associated with the physical activity signal 200 crossing a physical activity level threshold be removed from the physical activity calculation. There are three transition periods depicted in the example graph shown in FIG. 10, each having a duration threshold of t1, e.g., about 30 seconds to about 90 seconds. The total activity calculation for the example signal 200 shown in FIG. 10 can exclude the transition periods labeled t1.

In addition and in accordance with this disclosure, it may be desirable to exclude other portions of the activity level signal 200 from the total activity calculation. For example, it may be desirable to exclude portions of an activity level signal 200 above a specified threshold, e.g., to exclude higher levels. As one example, in FIG. 10, the total activity calculation can exclude the physical activity level signal within the time period labeled t3, which is above the second (upper) threshold Y mG. Thus, the activity level time for calculating total activity in FIG. 10 equals t2+t4, with the signal 200 within the transition periods having a duration threshold t1 removed and the signal 200 above the second threshold Y mG having a duration t3 removed.

Figure 11:
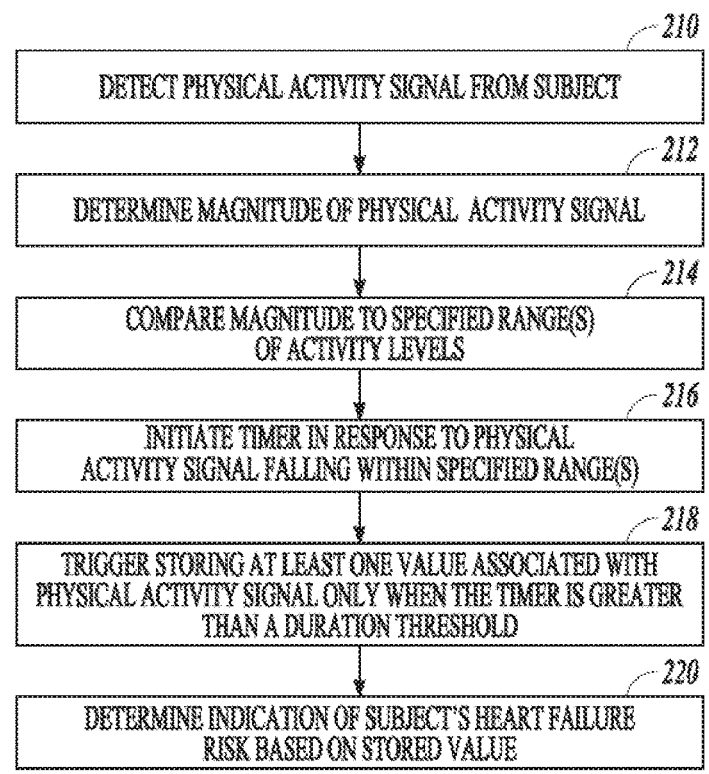
FIG. 11 is a flow diagram of another example of a technique for monitoring physical activity of a patient, in accordance with this disclosure.

FIG. 11 is a flow diagram of another example of a technique for monitoring physical activity of a patient, in accordance with this disclosure. More particular, FIG. 11 illustrates an example technique for monitoring physical activity of a patient using two or more activity level thresholds, like in FIG. 10.

In FIG. 11, a physical activity sensor, e.g., physical activity sensor 44 of FIG. 5 such as an accelerometer, can detect a physical activity of a subject and generate a physical activity signal representing the physical activity (block 210). At block 212, a processor, e.g., physiological signal processor circuit 42 of FIG. 5, can determine a magnitude of the physical activity signal and can compare the magnitude to one or more specified ranges of activity levels (block 214). For example, the processor can compare the determined magnitude to a range of X mG to Y mG, as in FIG. 10. In response to detecting that the determined magnitude falls within a specified range, the processor circuit can initiate a timer (block 216), e.g., using timing circuit 46 of FIG. 5, and trigger storing in a memory, e.g., memory circuit 48 of FIG. 5, at least one value associated with the physical activity signal, e.g., an amount of time determined by the timer and/or the magnitude associated with the detected physical activity signal, only when the timer is greater than the duration threshold, e.g., about 30 seconds to about 90 seconds (block 218). For example, the processor circuit may store pairs of data points in memory, in particular an amount of time that a subject spent at an activity level and the magnitude of the activity level. The processor circuit can then determine an indication of the subject's cardiovascular disease, e.g., heart failure risk or status, risk of decompensating, patient health, etc., based on the stored value including determining whether the subject is in one of at least two risk groups (block 220). For example, the processor circuit 42 can determine that the subject is in one of two or more physical activity groups, which is an indication of the subject's cardiovascular disease, e.g., heart failure risk. In one example, the processor can determine that the subject is in one of three physical activity groups: a low physical activity group, a medium physical activity group, or a high physical activity group, which is an indication of the subject's risk, e.g., of heart failure. It may be desirable to include more stratification and provide more than three physical activity groups. In another example, the processor circuit 42 can determine a risk percentage.

In some example implementations, triggering storing at least one value associated with the detected physical activity signal only when the timer is greater than a duration threshold can include accumulating an amount of time using the timer only when the magnitude of the detected physical activity signal falls within a specified range of physical activity level(s) for the duration threshold (and not when the magnitude of the detected physical activity signal falls within the specified range for less than the duration threshold).

In some example implementations that include multiple "bins" defined by a plurality of activity level thresholds, e.g., X mG, Y mG, Z mG, etc., the technique of FIG. 11 can include comparing, using the processor circuit, the magnitude of the detected physical activity signal to a plurality of specified ranges, where triggering storing at least one value associated with the detected physical activity signal falling within one of the specified ranges when the timer is greater than a duration threshold includes accumulating an amount of time using the timer only when the magnitude of the detected physical activity signal falls within one of the specified ranges for the duration threshold (and not when the magnitude of the detected physical activity signal falls within one of the specified ranges for less than the duration threshold).

Using the various techniques described above, the physical activity of a subject can be more accurately determined. In turn, patient monitoring can be adjusted accordingly, e.g., seen every 3 months instead of yearly, which can improve patient outcomes.

ADDITIONAL NOTES AND EXAMPLES

Example 1 includes subject matter (such as a system or apparatus) comprising: an activity sensor configured to detect a physical activity signal from the subject; and a physiological signal processor circuit configured to: determine a magnitude of the physical activity signal; initiate a timer in response to determining the magnitude of the physical activity signal exceeding an activity level threshold; trigger storing at least one value associated with the physical activity signal only when the magnitude of the physical activity signal exceeds the activity level threshold and the timer is greater than a duration threshold; and determine an indication of the subject's cardiovascular disease based on the stored value.

In Example 2, the subject matter of Example 1 optionally includes wherein the processor circuit configured to trigger storing at least one value associated with the physical activity signal only when the magnitude of the physical activity signal exceeds the activity level threshold and the timer is greater than a duration threshold is configured to: accumulate an amount of time using the timer only when the magnitude of the physical activity signal exceeds the activity level threshold for the duration threshold.

In Example 3, the subject matter of one or more combinations of Examples 1 and 2 optionally includes wherein the duration threshold is between about 30 seconds and about 90 seconds.

In Example 4, the subject matter of one or more combinations of Examples 1-3 optionally includes wherein the accumulated time includes the duration threshold.

In Example 5, the subject matter of one or more combinations of Examples 1-4 optionally includes wherein the activity level threshold is between about 10 mG (0.0981 m/s$^2$) and about 50 mG (0.4905 m/s$^2$).

In Example 6, the subject matter of one or more combinations of Examples 1-5 optionally includes wherein the processor circuit is configured to: compare the magnitude of the physical activity signal to a specified range of activity levels, and wherein the processor circuit configured to initiate a timer in response to detecting the magnitude of the physical activity signal exceeding an activity level threshold is configured to: initiate a timer in response to detecting the magnitude of the physical activity signal falling within the specified range of activity levels.

In Example 7, the subject matter of one or more combinations of Examples 1-6 optionally includes wherein the processor circuit configured to compare the magnitude of the detected physical activity signal to a specified range of activity levels is configured to compare the magnitude of the detected physical activity signal to a plurality of specified ranges defined by a plurality of activity level thresholds, wherein the processor circuit configured to trigger storing at least one value associated with the physical activity signal only when the magnitude of the physical activity signal exceeds the activity level threshold and the timer is greater than a duration threshold is configured to: accumulate an amount of time using the timer only when the magnitude of the physical activity signal falls within one of the plurality of specified ranges for the duration threshold.

In Example 8, the subject matter of one or more combinations of Examples 1-7 optionally includes wherein the duration threshold is a first duration threshold, and wherein the processor circuit configured to trigger storing at least one value associated with the physical activity signal only when the magnitude of the physical activity signal exceeds the activity level threshold and the timer that is greater than the duration threshold is configured to: for a period of time, trigger storing at least one of an amount of time and the magnitude associated with the physical activity signal, the processor circuit further configured to: for a plurality of stored magnitudes of physical activity level signals, determine a maximum magnitude if the time associated with the stored magnitude has exceeded a second duration threshold, and wherein the processor circuit configured to determine an indication of the subject's cardiovascular disease based on the stored value is configured to: determine an indication of the subject's heart failure risk based on the stored maximum magnitude.

In Example 9, the subject matter of one or more combinations of Examples 1-8 optionally includes wherein the second duration threshold is between about 0 minutes and about 10 minutes.

In Example 10, the subject matter of one or more combinations of Examples 1-9 optionally includes at least one physiological sensor other than the activity sensor to detect at least one physiological signal other than activity, wherein the processor circuit is configured to confirm that the subject is active based on a detected increase in the detected at least one physiological signal.

Example 11 can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter, comprising: detecting, using an activity sensor, a physical activity signal from a subject; determining, using a physiological signal processor circuit, a magnitude of the physical activity signal; initiating a timer in response to detecting the magnitude of the physical activity signal exceeding an activity level threshold; triggering storing at least one value associated with the physical activity signal only when the magnitude of the physical activity signal exceeds the activity level threshold and the timer is greater than a duration threshold; and determining, using the processor circuit, an indication of the subject's cardiovascular disease based on the stored value.

In Example 12, the subject matter of Example 11 optionally includes wherein triggering storing at least one value associated with the physical activity signal only when the magnitude of the physical activity signal exceeds the activity level threshold and the timer is greater than a duration threshold includes: accumulating an amount of time using the timer only when the magnitude of the detected physical activity signal exceeds the activity level threshold for the duration threshold.

In Example 13, the subject matter of one or more combinations of Examples 11-12 optionally includes wherein the duration threshold is between about 30 seconds and about 90 seconds.

In Example 14, the subject matter of one or more combinations of Examples 11-13 optionally includes wherein the accumulated time includes the duration threshold.

In Example 15, the subject matter of one or more combinations of Examples 11-14 optionally includes wherein the activity level threshold is between about 10 mG (0.0981 m/s$^2$) and about 50 mG (0.4905 m/s$^2$).

In Example 16, the subject matter of one or more combinations of Examples 11-15 optionally includes comparing the magnitude of the physical activity signal to a specified range of activity levels, wherein initiating a timer in response to detecting the magnitude of the physical activity signal exceeding an activity level threshold includes: initiating a timer in response to detecting the magnitude of the physical activity signal falling within the specified range of activity levels.

In Example 17, the subject matter of one or more combinations of Examples 11-16 optionally includes wherein comparing the magnitude of the detected physical activity signal to a specified range of activity levels includes comparing the magnitude of the detected physical activity signal to a plurality of specified ranges defined by a plurality of activity level thresholds, wherein triggering storing at least one value associated with the physical activity signal only when the magnitude of the physical activity signal exceeds the activity level threshold and the timer is greater than a duration threshold includes: accumulating an amount of time using the timer only when the magnitude of the physical activity signal falls within one of the plurality of specified ranges for the duration threshold.

In Example 18, the subject matter of one or more combinations of Examples 11-17 optionally includes wherein the duration threshold is a first duration threshold, and wherein triggering storing at least one value associated with the physical activity signal only when the magnitude of the physical activity signal exceeds the activity level threshold and the timer that is greater than the duration threshold includes: for a period of time, trigger storing at least one of an amount of time and the magnitude associated with the physical activity signal, the method comprising: for a plurality of stored magnitudes of physical activity level signals, determining a maximum magnitude if the time associated with the stored magnitude has exceeded a second duration threshold, and wherein determining an indication of the subject's cardiovascular disease based on the stored value includes: determining an indication of the subject's heart failure risk based on the stored maximum magnitude.

In Example 19, the subject matter of one or more combinations of Examples 11-18 optionally includes detecting, using at least one physiological sensor other than the activity sensor, an increase in at least one physiological signal other than activity to confirm that the subject is active.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
    an activity sensor configured to detect a physical activity signal from a subject; and
    a physiological signal processor circuit configured to:
        determine a magnitude of the physical activity signal;
        initiate a timer in response to determining the magnitude of the physical activity signal exceeding an activity level threshold;
        trigger storing at least one value associated with the physical activity signal only when the magnitude of the physical activity signal exceeds the activity level threshold and the timer is greater than a duration threshold; and
        determine an indication of the subject's cardiovascular disease based on the stored value.

2. The system of claim 1, wherein the duration threshold is between about 30 seconds and about 90 seconds.

3. The system of claim 1, wherein the activity level threshold is between about 0.0981 m/s$^2$ and about 0.4905 m/s$^2$.

4. The system of claim 1, wherein the processor circuit is configured to:
    compare the magnitude of the physical activity signal to a specified range of activity levels, and
    wherein the processor circuit configured to initiate a timer in response to detecting the magnitude of the physical activity signal exceeding an activity level threshold is configured to:

initiate a timer in response to detecting the magnitude of the physical activity signal falling within the specified range of activity levels.

5. The system of claim 4,
wherein the processor circuit configured to compare the magnitude of the detected physical activity signal to a specified range of activity levels is configured to compare the magnitude of the detected physical activity signal to a plurality of specified ranges defined by a plurality of activity level thresholds,
wherein the processor circuit configured to trigger storing at least one value associated with the physical activity signal only when the magnitude of the physical activity signal exceeds the activity level threshold and the timer is greater than a duration threshold is configured to:
accumulate an amount of time using the timer only when the magnitude of the physical activity signal falls within one of the plurality of specified ranges for the duration threshold.

6. The system of claim 5,
wherein the duration threshold is a first duration threshold, and wherein the processor circuit configured to trigger storing at least one value associated with the physical activity signal only when the magnitude of the physical activity signal exceeds the activity level threshold and the timer is greater than the duration threshold is configured to:
for a period of time, trigger storing at least one of an amount of time and the magnitude associated with the physical activity signal, the processor circuit further configured to:
for a plurality of stored magnitudes of physical activity level signals, determine a maximum magnitude if the time associated with the stored magnitude has exceeded a second duration threshold, and
wherein the processor circuit configured to determine an indication of the subject's cardiovascular disease based on the stored value is configured to:
determine an indication of the subject's heart failure risk based on the stored maximum magnitude.

7. The system of claim 6, wherein the second duration threshold is between about 0 minutes and about 10 minutes.

8. The system of claim 1, comprising:
at least one physiological sensor other than the activity sensor to detect at least one physiological signal other than activity,
wherein the processor circuit is configured to confirm that the subject is active based on a detected increase in the detected at least one physiological signal.

9. The system of claim 1, wherein the processor circuit is configured to:
for a plurality of stored magnitudes of physical activity level signals, determine a maximum of the plurality of stored magnitudes having a time associated with the stored magnitude exceeding a second duration threshold, and
wherein, to determine the indication of the subject's cardiovascular disease based on the stored value, the processor circuit is configured to:
determine an indication of the subject's heart failure risk based on the stored maximum magnitude.

10. A method comprising:
detecting, using an activity sensor, a physical activity signal from a subject;
determining, using a physiological signal processor circuit, a magnitude of the physical activity signal;
initiating a timer in response to determining the magnitude of the physical activity signal exceeding an activity level threshold;
triggering storing at least one value associated with the physical activity signal only when the magnitude of the physical activity signal exceeds the activity level threshold and the timer is greater than a duration threshold; and
determining, using the processor circuit, an indication of the subject's cardiovascular disease based on the stored value.

11. The method of claim 10, comprising:
comparing the magnitude of the physical activity signal to a specified range of activity levels,
wherein initiating a timer in response to detecting the magnitude of the physical activity signal exceeding an activity level threshold includes:
initiating a timer in response to detecting the magnitude of the physical activity signal falling within the specified range of activity levels.

12. The method of claim 11,
wherein comparing the magnitude of the detected physical activity signal to a specified range of activity levels includes comparing the magnitude of the detected physical activity signal to a plurality of specified ranges defined by a plurality of activity level thresholds,
wherein triggering storing at least one value associated with the physical activity signal only when the magnitude of the physical activity signal exceeds the activity level threshold and the timer is greater than a duration threshold includes:
accumulating an amount of time using the timer only when the magnitude of the physical activity signal falls within one of the plurality of specified ranges for the duration threshold.

13. The method of claim 10, wherein the duration threshold is a first duration threshold, and wherein triggering storing at least one value associated with the physical activity signal only when the magnitude of the physical activity signal exceeds the activity level threshold and the timer that is greater than the duration threshold includes:
for a period of time, trigger storing at least one of an amount of time and the magnitude associated with the physical activity signal, the method comprising:
for a plurality of stored magnitudes of physical activity level signals, determining a maximum magnitude if the time associated with the stored magnitude has exceeded a second duration threshold, and
wherein determining an indication of the subject's cardiovascular disease based on the stored value includes:
determining an indication of the subject's heart failure risk based on the stored maximum magnitude.

14. The method of claim 10, comprising:
for a plurality of stored magnitudes of physical activity level signals, determining a maximum of the plurality of stored magnitudes having a time associated with the stored magnitude exceeding a second duration threshold, and
wherein determining the indication of the subject's cardiovascular disease based on the stored value comprises:
determining an indication of the subject's heart failure risk based on the stored maximum magnitude.

15. A system comprising:
means for detecting a physical activity signal from a subject;

means for determining a magnitude of the physical activity signal;
means for initiating a timer in response to detecting the magnitude of the physical activity signal exceeding an activity level threshold;
means for triggering storing at least one value associated with the physical activity signal only when the magnitude of the physical activity signal exceeds the activity level threshold and the timer is greater than a duration threshold; and
means for determining an indication of the subject's cardiovascular disease based on the stored value.

16. The system of claim 15, comprising:
for a plurality of stored magnitudes of physical activity level signals, means for determining a maximum of the plurality of stored magnitudes having a time associated with the stored magnitude exceeding a second duration threshold, and
wherein the means for determining the indication of the subject's cardiovascular disease based on the stored value comprises:
    means for determining an indication of the subject's heart failure risk based on the stored maximum magnitude.

* * * * *